Figure 1:
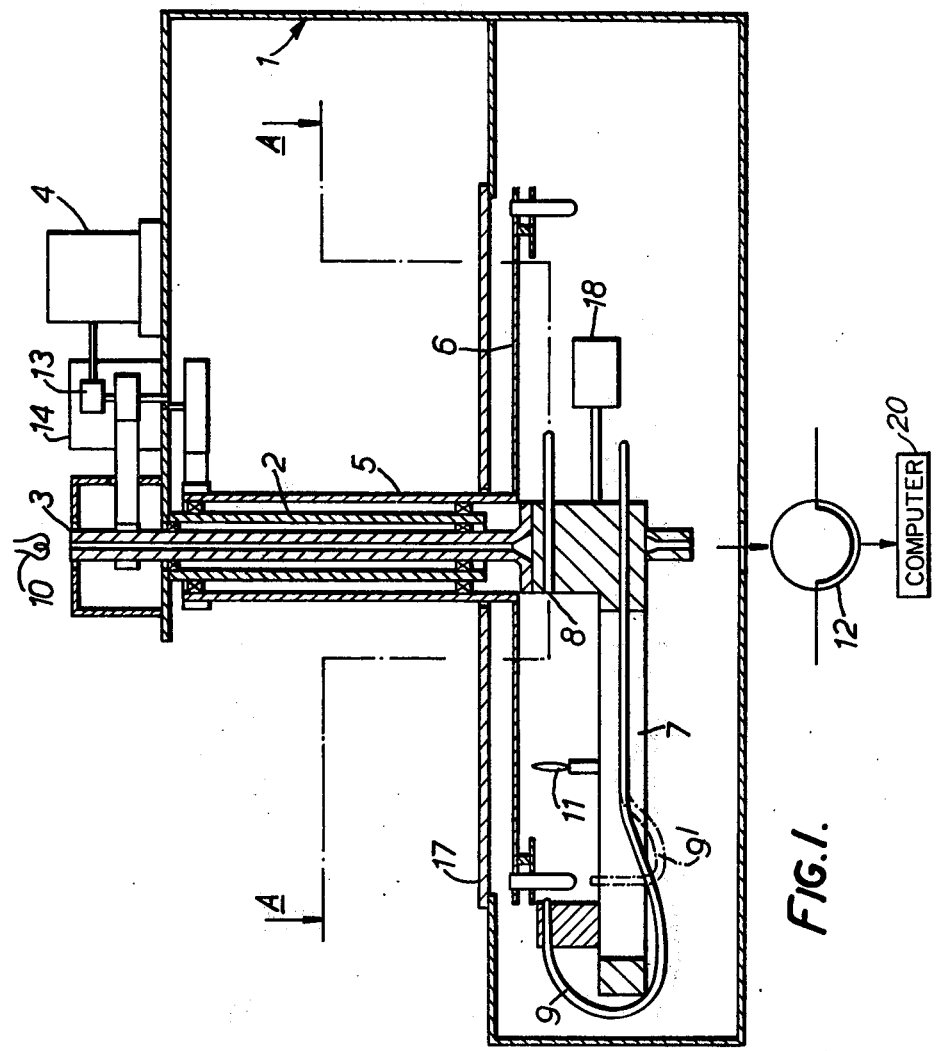

United States Patent [19]
Greaves et al.

[11] 3,966,322
[45] June 29, 1976

[54] DEVICE FOR USE IN PRODUCING A SCANNING BEAM OF RADIATION AND APPARATUS FOR USE IN INVESTIGATING SPECIMENS

[75] Inventors: Geoffrey Stuart Greaves; Ian Deverill; Roger Abraham Bunce, all of Birmingham, England

[73] Assignee: Vickers Limited, London, England

[22] Filed: Nov. 6, 1974

[21] Appl. No.: 521,254

[30] Foreign Application Priority Data
Nov. 8, 1973 United Kingdom............... 51988/73
Oct. 28, 1974 United Kingdom............... 46608/74

[52] U.S. Cl................................ 356/39; 23/253 R; 250/227; 356/40; 356/180; 356/201
[51] Int. Cl.²................... G01N 33/16; G01N 21/24
[58] Field of Search ............... 356/39, 40, 180, 184, 356/195, 201, 208, 41; 250/227, 231 R, 231 SE; 23/253 R

[56] References Cited
UNITED STATES PATENTS

| | | |
|---|---|---|
| 3,390,274 | 6/1968 | Hunt .............................. 250/231 R |
| 3,461,856 | 8/1969 | Polanyi ........................... 356/41 X |
| 3,480,786 | 11/1969 | Kottman ......................... 250/227 X |
| 3,567,393 | 3/1971 | Welch.............................. 356/39 X |
| 3,817,632 | 6/1974 | Picunko et al....................... 356/39 |
| 3,831,169 | 8/1974 | Raser ........................ 250/231 SE X |

*Primary Examiner*—Alfred E. Smith
*Assistant Examiner*—E. R. LaRoche
*Attorney, Agent, or Firm*—Reed Smith Shaw & McClay

[57] ABSTRACT

A device for use in producing a scanning beam of radiation comprises a rotor member carrying two optical wave guides arranged so as to direct light along the rotary axis of the rotor member, then radially outwardly to pass from one wave guide to the other, then radially inwardly and finally along the said rotary axis again.

When the device is adapted for investigating liquid samples, a turntable, carrying a number of vials containing liquid samples at spaced locations around its periphery, is rotated in indexing fashion and, during each dwell period of the turntable, the rotor member is rotated so that the circularly scanning beam of light leaving the first mentioned wave guide scans each of the vials in turn at least once.

24 Claims, 5 Drawing Figures

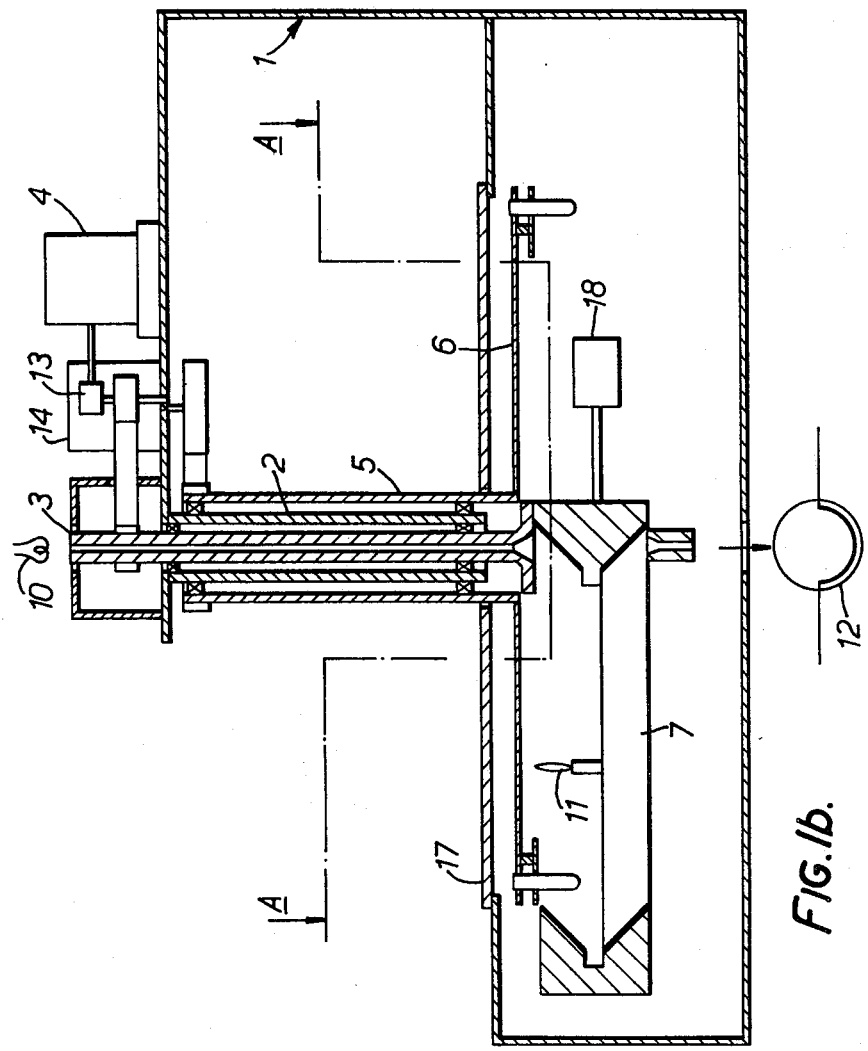

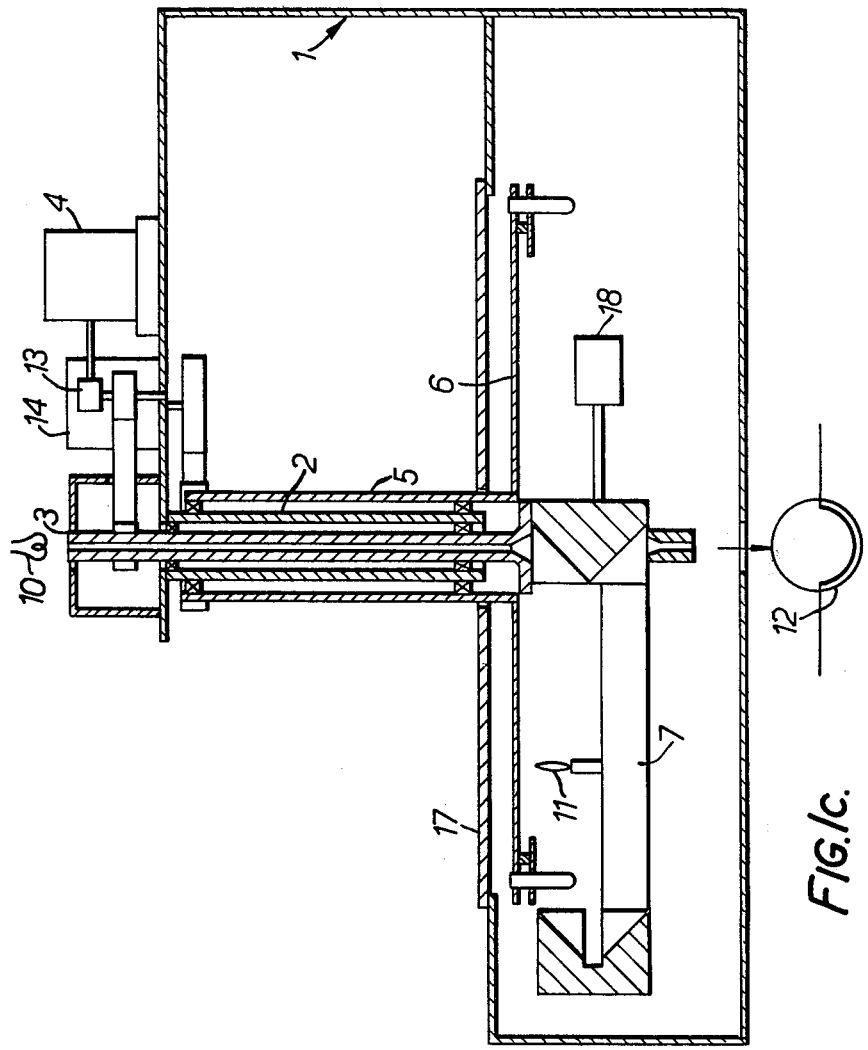

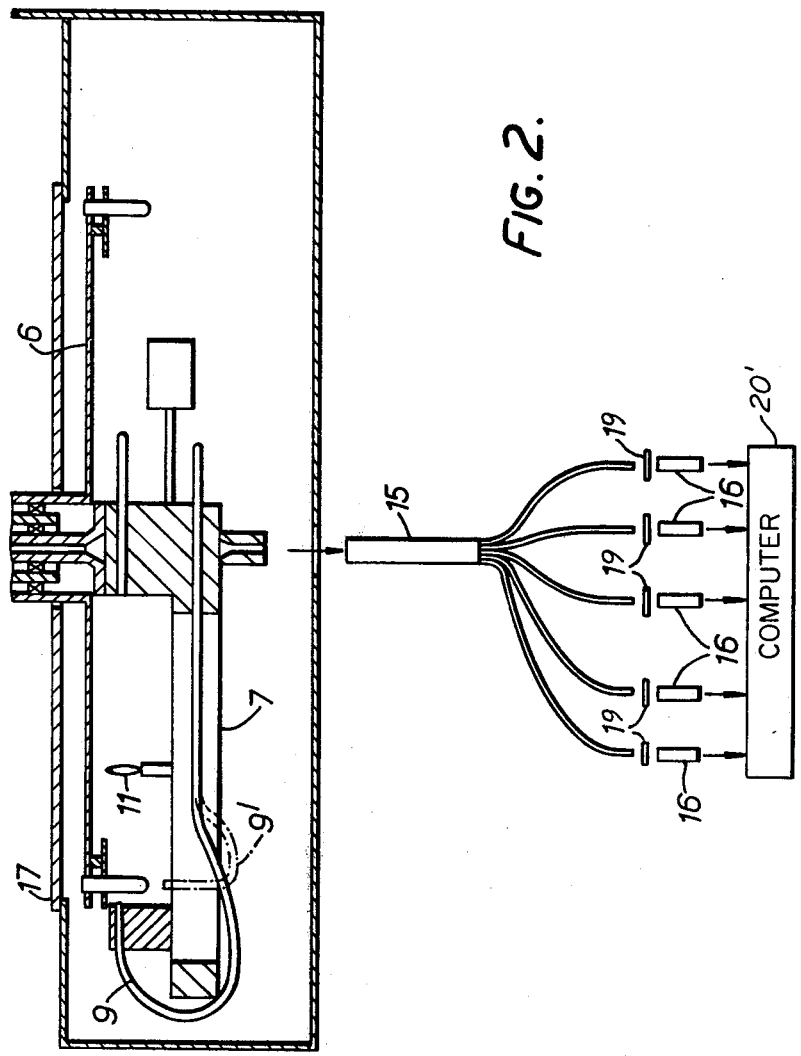

DEVICE FOR USE IN PRODUCING A SCANNING BEAM OF RADIATION AND APPARATUS FOR USE IN INVESTIGATING SPECIMENS

This invention relates to devices for use in producing scanning beams of radiation and to apparatus for use in investigating specimens.

According to one aspect of the present invention there is provided a device for use in producing a scanning beam of radiation, comprising a rotor member mounted for rotation about a predetermined rotational axis and extending transversely with respect to that axis, first radiation guide means carried by the said rotor member and having an input portion which extends substantially along the said rotational axis from an input aperture positioned substantially thereon, an output portion which extends in a predetermined direction with respect to the rotational axis and terminates in an output aperture which is spaced therefrom, and an intermediate portion which connects the input portion to the output portion, and the device also comprising second radiation guide means carried by the rotor member and having an input portion which extends in a predetermined direction with respect to the rotational axis from an input aperture which is spaced therefrom and which input portion is so arranged as to receive, in use, radiation from the output portion of the first radiation guide means, an output portion which extends substantially along the said rotational axis and terminates in an output aperture positioned substantially thereon, and an intermediate portion which connects the input and output portions of the second radiation guide means.

According to another aspect of the invention there is provided apparatus for use in investigating specimens, comprising a carrier having, or adapted to support, a plurality of at least partially light-transmitting vessels each for containing a specimen, means for advancing the carrier stepwise in a predetermined direction, means for directing radiation, at least once during each dwell period of the carrier between successive stepwise advancements of the carrier, at each of the vessels in turn, and radiation receiving means arranged to receive radiation leaving the vessels.

Preferably, the apparatus is for use in investigating liquid specimens and comprises a turntable having a rotational axis and having, or adapted to support, a plurality of at least partially light-transmitting vials or other vessels, each for containing a liquid specimen to be investigated, in a circular array centred on the said axis, means for rotating the turntable stepwise about the said axis, means for directing radiation, at least once during each dwell period of the turntable between successive stepwise advancements of the turntable, at each of the vessels in turn, and radiation receiving means arranged to receive radiation leaving the vessels.

Generally, the radiation would be optical, in which case the first and second radiation guide means, or the radiation directing means and radiation receiving means, would preferably comprise respective fibre light guides but could alternatively comprise prisms or mirrors defining light paths. By "optical" radiation is intended to be understood radiation of wavelength greater than X-rays but less than microwaves, i.e. including infrared and ultra-violet radiation as well as visible radiation.

Figure 1A:
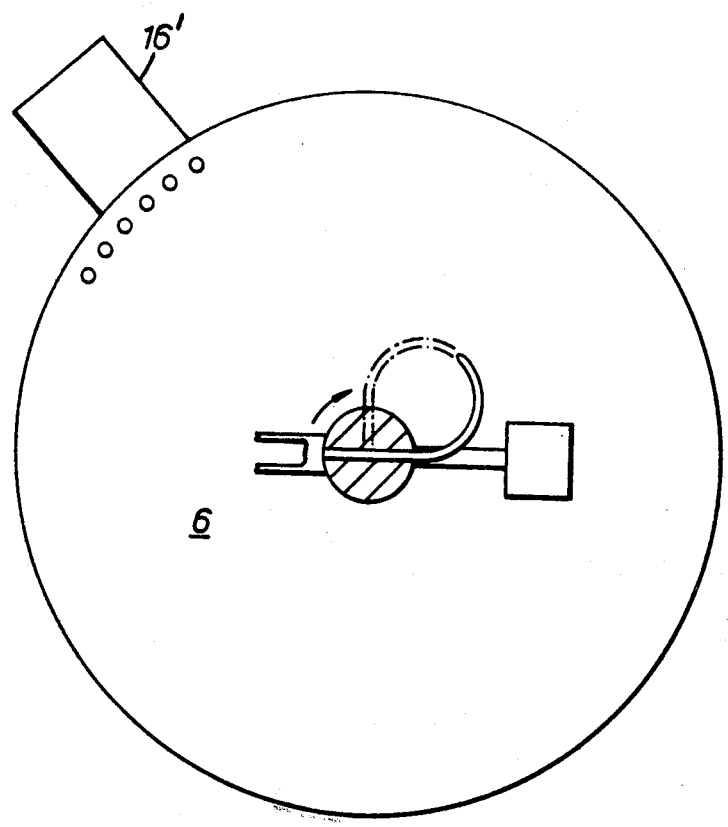

For a better understandng of the invention, and to show how the same may be carried into effect, reference will now be made, by way of example, to the accompanying drawings, in which:

FIG. 1 shows a vertical sectional view of apparatus forming part of an automatic blood analysing machine, FIG. 1a shows a horizontal sectional view of the machine taken on the line A—A of FIG. 1, FIGS. 1b and 1c show modifications of the embodiment shown in FIG. 1 comprising a mirror and prism system, respectively, and FIG. 2 shows a view similar to FIG. 1 of a modification of the machine.

The machine illustrated in FIGS. 1 and 1a is used for colorimetric, light scattering and fluorimetric evaluation of reactions between samples of blood and reagent(s), and comprises a stationary frame 1 which carries a hollow vertical trunnion 2. Extending coaxially inside the trunnion 2 is a hollow rotatable shaft 3 which is connected at its upper end by a pulley and belt arrangement and a gearbox 13 to an electric motor 4 mounted on the frame 1. The trunnion 2 is surrounded coaxially by a further rotatably shaft 5 which carries a horizontal table 6 at its lower end and is connected at its upper end by a further pulley and belt arrangement to a second electric motor 14, which is a stepping motor.

The table 6, which is covered by a stationary cover 17, is circular, its centre being on the common axis of the trunnion 2 and the shafts 3 and 5, and has about its periphery a plurality of equally spaced vials. Mose desirably, these vials are fixed relative to the table 6 but they may alternatively be removably fitted into notches in the table. Each vial extends downwardly from the level of the table into the interior of the frame 1. The shaft 3 is connected at its lower end, which is below the table 6, to a horizontal arm 7 which extends radially with respect to the shaft 3. The shaft is also connected to a counterbalance 18 for the arm 7. The arm 7 carries two fibre optic light guides 8 and 9. The light guide 8 has an input end at the upper end of the shaft 3 and extends vertically downwards, coaxially within the shaft 3. At the lower end of the shaft 3 the guide 8 extends therefrom radially outwardly along the arm 7 and has an output end at a position along the arm which is inward of the periphery of the table 6. The output end of the guide 8 defines a slit-form output aperture. The guide 9 has an input end which is mounted on the arm 7 outward of the periphery of the table and aligned with the end of the guide 8. The input end of the guide 9 defines a slit-form input aperture. The guide 9 extends from the periphery of the table radially inwards along the arm 7 and has an output end which is directed vertically downwards along the axis of the shaft 3. FIG. 1a shows how the light guides are looped between their radial and axial portions in order to avoid imposing excessive curvature on the guides.

Above the upper end of the shaft 3 is a lamp 10 arranged to direct light vertically downwards into a circular input aperture defined by the input end of the light guide 8. Between the lamp 10 and the input aperture may be mounted a filter or grating unit for selecting the wavelength of light entering the input aperture and thereby enabling different reactions to be evaluated. Radially outwardly of the output end of the guide 8 is an optical system comprising a correction slit (not shown), converging lens 11 and a further correction slit (not shown), for focusing light delivered by the guide 8 on liquid in a vial. The optical system is clamped to a horizontal slideway, formed in the arm 7, to facilitate adjustment. Light which is transmitted by the liquid is received by the guide 9 at its input end and is delivered to its output end from which it is directed vertically downwards, along the axis of the shaft 3, to a photomultiplier 12.

When the blood analysing machine is in operation, the table 6 is rotated stepwise by the motor 14 past a dispensing station 16', whereat a sample of blood and a quantity of reagent (and possibly also diluent and/or dye) is placed in a different vial during each dwell period of the table 6 between successive stepwise rotational advancements of the table. At the same time, the motor 4 is caused to rotate the shaft 3 through at least one revolution during each dwell period, thus causing the arm 7 to rotate so that the light beam from the light guide 9 scans the vials in succession and the light transmitted by the liquids in the vials is received by the light guide 9 and passed to the photomultiplier 12 which provides an output voltage, the magnitude of which depends upon the intensity of light received by the guide 9. The photomultiplier 12 is connected to a computer 20 which stores a set of data for revolution of the shaft 3, representing the output voltage of the photomultiplier 12 for each of the vials. When the shaft 3 is rotated at least twice during each dwell period, the computer uses the several sets of data to form a mean value for the output voltage of the photomultiplier in respect of each vial. In practice, it is more convenient to rotate the motor 4 continuously rather than for it to rotate only during each dwell period of the table 6. Then, the computer is arranged so as to disregard the data received during each stepwise rotational advancement of the table 6 between successive dwell periods. Furthermore, the computer 20 so arranged that if during each dwell period the shaft 3 rotates through a non-integral number of revolutions the computer accepts data only for the nearest integral number of revolutions of the shaft, below the actual number of revolutions undergone.

In the circumstances, therefore, the illustrated machine is used for colorimetric analysis of the blood samples. By making a slight modification, however, the machine may be used for light scattering or fluorimetric analysis of the blood samples. The modification is shown in broken lines in FIG. 1 and entails replacing the light guide 9 by a guide 9' whose input end is vertically below the vial and perpendicular to the output end of the guide 8 and placing a colour filter between the output end of the light 9' and the photomultiplier 12. Then the output voltage of the photomultiplier depends upon the intensity with which light from the guide 8 in a selected wavelength band, predetermined by the filter, leaves the vial.

In FIG. 2 of the drawings a further modification is shown which enables the intensity of light collected from the vials in each of several different wavelengths bands to be determined. The light from the output end of the light guide 9 or 9' is delivered to the input end of a further fibre optic light guide 15 which is fixed relative to the frame 1. Downstream of its input end the light guide 15 is divided into several different bundles directed towards respective photomultipliers 16, each bundle being provided at its output end with a different colour filter 19. Thus, each photomultiplier 16 provides an output voltage the magnitude of which depends upon the intensity of light received by the light guide 15 in the wavelength band of the filter concerned, and the photomultipliers are connected to the computer 20' which stores data representing the output voltage of each photomultiplier for each of the vials.

Just as each of the fibre optical light guides 8 and 9 and 9' may be replaced by a mirror or prism system as shown in FIGS. 1b and 1c, respectively, so also may the guide 15 be replaced by a mirror or prism beam-dividing system.

It will be appreciated that the illustrated apparatus enables a circularly scanning beam to be produced without moving the lamp 10, and to apply light collected from a circularly-scanned region to the photomultiplier 12 or the photomultipliers 16 without moving the photomultiplier(s).

It is not essential that the input end of the guide 8 and the output end of the guide 9 or 9' should be on opposite axial sides of the arm 7, since by making the end of one guide annular surrounding the end of the other guide, the light could enter and leave the guides on the same side of the arm.

We claim:

1. Apparatus for use in investigating specimens, comprising a carrier adapted to support a plurality of at least partially light-transmitting vessels each for containing a specimen, means for advancing the carrier stepwise in a predetermined direction, means for directing radiation, at least once during each dwell period of the carrier between successive stepwise advancements of the carrier, at each of the vessels in turn, and radiation receiving means arranged to receive radiation leaving the vessels.

2. Apparatus for use in investigating liquid specimens, comprising a turntable having a rotational axis and adapted to support a plurality of at least partially light-transmitting vials or other vessels, each for containing a liquid specimen to be investigated, in a circular array centred on said axis, means for rotating the turntable stepwise about said axis, means for directing radiation, at least once during each dwell period of the turntable between successive stepwise advancements of the turntable, at each of the vessels in turn, and radiation receiving means arranged to receive radiation leaving the vessels.

3. Apparatus as claimed in claim 2, wherein the stepwise rotating means comprises a stepping motor and a drive connection between the motor and the turntable.

4. Apparatus as claimed in claim 3, wherein the radiation directing means comprises a light source, a rotor member mounted to receive a beam of light from said source and for rotation about the said rotational axis and extending transversely with respect to that axis, drive means arranged to drive said rotor member, first radiation guide means carried by the said rotor member and having an input portion which extends substantially along the said rotational axis from an input aperture positioned substantially thereon, an output portion which extends in a predetermined direction with respect to the rotational axis and terminates in an output aperture which is spaced therefrom, and an intermediate portion which connects the input portion to the output portion, and wherein the radiation receiving means comprises second radiation guide means carried by the rotor member and having an input portion which extends in a predetermined direction with respect to the rotational axis from an input aperture which is spaced therefrom and which input portion is so arranged as to receive, in use, radiation from the output portion of the first radiation guide means, an output portion which extends substantially along the said rotational axis and terminates in an output aperture positioned substantially thereon, and intermediate portion which connects the input and output portions of the second radiation guide means, and a photodetector mounted to receive light which leaves the second radiation guide means by way of the output thereof and arranged to produce output signals which depend upon the intensity of received light.

5. Apparatus as claimed in claim 4, wherein the input portion of the first radiation guide means extends in the same direction along the said rotational axis from its input aperture as the output portion of the second radiation guide means extends towards its output aperture.

6. Apparatus as claimed in claim 4, wherein the said input portion of the first radiation guide means extends in the opposite direction along the said rotational axis from its input aperture with respect to the direction in which the output portion of the second radiation guide means extends towards its output aperture.

7. Apparatus as claimed in claim 4, wherein the output portion of the first radiation guide means extends radially away from the said rotational axis toward its output aperture.

8. Apparatus as claimed in claim 4, wherein the input portion of the second radiation guide means is aligned with and has its input aperture confronting the output aperture of the output portion of the first radiation guide means.

9. Apparatus as claimed in claim 4, wherein the input portion of the second radiation guide means extends substantially perpendicularly with respect to the output portion of the first radiation guide means, and the axis of that input portion intersects the axis of that output portion at a position which is beyond that output aperture and before that input aperture.

10. Apparatus as claimed in claim 4, wherein the first and second radiation guide means comprise repective fibre optic light guides.

11. Apparatus as claimed in claim 4, wherein the first and second radiation guide means comprise respective trains of prisms.

12. Apparatus as claimed in claim 4, wherein the first and second radiation guide means comprise respective trains of mirrors.

13. Apparatus as claimed in claim 4, wherein computer means are provided for correlating output signals produced, in use, by the photodetector with the instantaneous angular position of the beam of light about the said rotational axis.

14. Apparatus for use in carrying out colorimetric analysis of a plurality of specimens and as claimed in claim 4, wherein the input portion of the second radiation guide means is arranged to receive light emanating from the output portion of the first radiation guide means and transmitted by the specimens.

15. Apparatus for use in carrying out light scattering or fluorimetric analyses of a plurality of specimens and as claimed in claim 4, wherein the input portion of the second radiation guide means is arranged to receive light emanating from the output portion of the first radiation guide means and deviated by the specimens, and wherein a colour filter is mounted between the output aperture, of the output portion of the second radiation guide means, and the photodetector for preventing light, except that which lies in a wavelength band predetermined by the filter, from reaching the photodector.

16. Apparatus as claimed in claim 4, comprising third radiation guide means mounted stationarily in the apparatus to receive light which leaves the second radiation guide means and to divide such light into first and second beams directed along respective paths to the said photodetector and to a second photodetector, and first and second colour filters, disposed in the respective paths for blocking light, except that which lies in respective first and second wavelength bands predetermined by the filters, so that when the apparatus is in use each photodetector produces output signals which depend upon the intensity with which light, in the first or second predetermined wavelength band, leaves the vessels.

17. Apparatus for use in carrying out colorimetric analysis of a plurality of specimens, comprising a rotor member mounted for rotation about a predetermined rotational axis and extending transversely with respect to that axis; first radiation guide means carried by the said rotor member and having an input portion which extends substantially along the said rotational axis from an input aperture positioned substantially thereon, an output portion which extends in a predetermined direction with respect to the rotational axis and terminates in an output aperture which is spaced therefrom, and an intermediate portion which connects the input portion to the output portion; second radiation guide means carried by the rotor member and having an input portion which extends in a predetermined direction with respect to the rotational axis from an input aperture which is spaced therefrom and which confronts the output aperture of the first radiation guide means, an output portion which extends substantially along the said rotational axis and terminates in an output aperture positioned substantially thereon, and an intermediate portion which connects the input and output portions of the second radiation guide means; a light source mounted to direct a beam of light into the said input portion of the first radiation guide means; a photodetector mounted to receive light which leaves the said radiation guide means by way of the output portion thereof; drive means for rotating the rotor member about the said rotational axis thereby to produce, when the apparatus is in use, a circularly scanning beam of light emanating from the output portion of the first radiation guide means; and a carrier having, or adapted to support, a plurality of at least partially light-transmitting vessels, each for containing a specimen to be analysed, in a circular array centred on the said rotational axis so that when the apparatus is in use the vessels are scanned by the circularly scanning beam of light and the photodetector produces output signals which depend upon the intensity with which light is transmitted by the specimens.

18. Apparatus as claimed in claim 17, further comprising computer means for correlating such output signals produced by the photodetector with the instantaneous angular position of the beam of light about the said rotational axis.

19. Apparatus as claimed in claim 17, wherein the first and second radiation guide means comprise respective fibre optic light guides.

20. Apparatus as claimed in claim 17, comprising third radiation guide means mounted stationarily in the apparatus to receive light which leaves the second radiation guide means and to divide such light into first and second beams directed along respective paths to the said photodetector and a second photodetector, and first and second colour filters, disposed in the respective paths for blocking light except that which lies in respective first and second wavelength bands predetermined by the filters, so that when the apparatus is in use each photodetector produces output signals which depend upon the intensity with which light, in the first or second predetermined wavelength band, leaves the vessels.

21. Apparatus for use in carrying out light scattering or fluorimetric analyses of a plurality of specimens, comprising a rotor member mounted for rotation about a predetermined rotational axis and extending transversely with respect to that axis; first radiation guide means carried by the said rotor member and having an input portion which extends substantially along the said rotational axis from an input aperture positioned substantially thereon, an output portion which extends in a predetermined direction with respect to the rotational axis and terminates in an output aperture which is spaced therefrom, and an intermediate portion which connects the input portion to the output portion; second radiation guide means carried by the rotor member and having an input portion, which extends in a predetermined direction with respect to the rotational axis from an input aperture which is spaced therefrom and which input portion extends substantially perpendicularly with respect to the output portion of the first radiation guide means which the axis of that input portion intersecting the axis of that output portion at a position which is beyond that output aperture and before that input aperture; an output portion which extends substantially along the said rotational axis and terminates in an output aperture positioned substantially thereon, and an intermediate portion which connects the input and output portions of the second radiation guide means; a light source mounted to direct a beam of light into the said input portion of the first radiation guide means; a photodetector mounted to receive light which leaves the second radiation guide means by way of the output portion thereof; a colour filter mounted between the said output aperture, of the output portion of the second radiation guide means, and the photodetector for preventing light, except that which lies in a wavelength band predetermined by the filter, from reaching the photodetector; drive means for rotating the rotor member about the said rotational axis, thereby to produce, when the apparatus is in use, a circularly scanning beam of light emanating from the output portion of the first radiation guide means; and a carrier having, or adapted to support, a pluraity of at least partially light-transmitting vessels, each for containing a specimen to be analysed, in a circular array centered on the said rotational axis, so that when the apparatus is in use the vessels are scanned by the circularly scanning beam of light and the photodetector produces output signals which depend upon the intensity with which light, in the predetermined wavelength band, leaves the vessels.

22. Apparatus as claimed in claim 21, further comprising computer means for correlatng such output signals produced by the photodetector with the instantaneous angular position of the beam of light about the said rotational axis.

23. Apparatus as claimed in claim 21, wherein the first and second radiation guide means comprise respective fibre optic light guides.

24. Apparatus as claimed in claim 21, comprising third radiation guide means mounted stationarily in the apparatus to receive light which leaves the second radiation guide means and to divide such light into a first beam directed along a first path to the said colour filter and the said photodetector and a second beam directed along a second path to a second colour filter, for blocking light except that which lies in a second wavelength band predetermined by the second filter, and a second photodetector so that when the apparatus is in use the second photodetector produces output signals which depend upon the intensity with which light, in the second predetermined wavelength band, leaves the vessels.

* * * * *

UNITED STATES PATENT OFFICE
CERTIFICATE OF CORRECTION

PATENT NO. : 3,966,322
DATED : June 29, 1976
INVENTOR(S) : Greaves, Deverill, Bunce It is certified that error appears in the above-identified patent and that said Letters Patent are hereby corrected as shown below:

Page 1, item [73] "Assignee": Change "Vickers Limited, London, England." to read -- Secretary of State for Social Services, London, England. --

Signed and Sealed this

Twenty-fifth Day of January 1977

[SEAL]

*Attest:*

RUTH C. MASON
*Attesting Officer*

C. MARSHALL DANN
*Commissioner of Patents and Trademarks*